United States Patent [19]

Spitzer

[11] 4,065,621
[45] Dec. 27, 1977

[54] PROCESS FOR 3-ALKYL AND 3-PHENYL CEPHALOSPORINS

[75] Inventor: Wayne Alfred Spitzer, Indianapolis, Ind.

[73] Assignee: Eli Lilly and Company, Indianapolis, Ind.

[21] Appl. No.: 720,180

[22] Filed: Sept. 3, 1976

Related U.S. Application Data

[62] Division of Ser. No. 576,818, May 12, 1975, Pat. No. 4,013,651.

[51] Int. Cl.$^2$ ............................................. C07D 501/04
[52] U.S. Cl. ...................................... 544/30; 424/246; 544/16
[58] Field of Search ................................... 260/243 C

[56] References Cited

U.S. PATENT DOCUMENTS 4,001,226  1/1977  Spry .................................. 260/243 C Primary Examiner—Nicholas S. Rizzo
Attorney, Agent, or Firm—William B. Scanlon; Everet F. Smith

[57] ABSTRACT

7-Amino-(or 7-acylamido)-3-(disubstituted-amino)-3-cephem-4-carboxylic acid esters are prepared with the corresponding 3-chloro-3-cephem ester or 3-alkyl-(or aryl)-sulfonyloxy-3-cephem esters and a secondary amine, e.g., diphenylmethyl 7-[2-(2-thienyl)acetamido]-3-morpholino-3-cephem-4-carboxylate is prepared with the corresponding 3-methyl-sulfonyloxy ester and morpholine. The 3-amino-substituted cephem esters are useful intermediates undergoing reduction with diborane to the corresponding 3H-3-cephem esters or, alternatively, they are reacted with Grignard reagents, e.g., phenylmagnesium bromide to provide, for example, the 3-phenyl-3-cephem ester.

5 Claims, No Drawings

PROCESS FOR 3-ALKYL AND 3-PHENYL CEPHALOSPORINS

This is a division of application Ser. No. 576,818, filed May 12, 1975, now U.S. Pat. No. 4,013,651.

SUMMARY

This invention relates to novel cephalosporin intermediates. In particular, this invention relates to 7-amino and 7-acylamido cephalosporin esters directly substituted on the 3-position of the dihydrothiazine ring of the cephem nucleus with a secondary acyclic amino group or a cyclic secondary amino group. The amino esters are prepared by reacting an acyclic or cyclic secondary amine with a 7-amino or 7-acylamide-3-chloro or 3-alkyl(or aryl)-sulfonyloxy-3-cephem ester. The amino esters can be reduced under anhydrous conditions with diborane to provide, via reductive removal of the amino group, a 3H-3-cephem carboxylic acid antibiotic.

Alternatively, the 3-amino cephalosporin esters provided herein can be reacted with an alkyl or aryl Grignard reagent to provide the corresponding 3-alkyl- or 3-aryl-3-cephem ester. Removal of the ester group from the product affords the known 3-alkyl or 3-phenyl cephalosporin antibiotic.

DETAILED DESCRIPTION

The 3-disubstituted-amino cephalosporin esters of this invention are represented by the following general formula I.

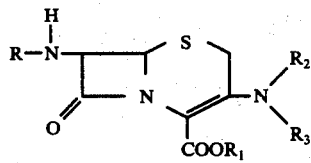

Formula I wherein
R is hydrogen or an acyl group

wherein
R' is $C_1$-$C_6$ alkyl, $C_1$-$C_3$ cyanoalkyl, phenyl, halophenyl, methylphenyl, hydroxyphenyl, nitrophenyl, aminophenyl, or methoxyphenyl; or
R' is a group of the formula

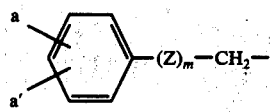

wherein
a and a' are independently hydrogen, $C_1$-$C_4$ alkyl, $C_1$-$C_4$ alkoxy, halogen, nitro, amino, or carboxy,
Z is O or S, and
m is 0 or 1; or
R' is a group of the formula

wherein

P is thienyl, phenyl, or a substituted phenyl group of the formula

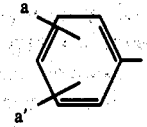

wherein
a and a' are as defined above,
Q is hydroxy, amino, carboxy, or —$SO_3H$; or
R' is a group of the formula

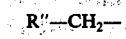

wherein
R'' is thienyl, furyl, 2-oxazalyl, 2-thiazolyl, or 1-tetrazalyl;
$R_1$ is benzyl, 4-nitrobenzyl, 4-methoxybenzyl, diphenylmethyl, t-butyl, or 2,2,2-trichloroethyl; and
$R_2$ and $R_3$ when taken separately are independently $C_1$-$C_4$alkyl, benzyl, or phenylethyl and when taken together with the attached nitrogen are pyrrolidino, piperidino, morpholino, thiomorpholino, or a 4-substituted piperazino group of the formula

wherein
$R_4$ is $C_1$-$C_4$ lower alkyl.

In the foregoing definition of the compounds provided by this invention, the term "$C_1$-$C_6$ alkyl" refers to the straight and branched chain alkyl hydrocarbon groups such as methyl, ethyl, n-propyl, isopropyl, n-butyl, sec-butyl, n-amyl, isoamyl, n-hexyl, and the like; "$C_1$-$C_3$ cyanoalkyl" refers to such groups as cyanomethyl, 2-cyanoethyl, 3-cyanopropyl, and 2-cyanopropyl: "$C_1$-$C_4$ lower alkyl" refers to the straight and branched chain lower alkyl hydrocarbon groups such as methyl, ethyl, n-propyl, iso-propyl, n-butyl, t-butyl, and the like; "$C_1$-$C_4$ lower alkoxy" refers to methoxy, ethoxy, isopropoxy, n-butoxy, and the like. As used herein, the term "halogen" refers to fluoro, chloro, bromo, and iodo.

Illustrative of the groups in the above definition represented by the following formula where m is 0 are

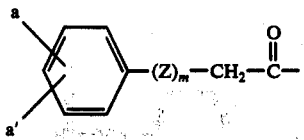

phenylacetyl, 4-methylphenylacetyl, 3-ethylphenylacetyl, 4-isopropylphenylacetyl, 2-methylphenylacetyl, 4-chlorophenylacetyl, 4-nitrophenylacetyl, 4-bromophenylacetyl, 2,4-dichlorophenylacetyl, 3-bromophenylacetyl, 4-iodophenylacetyl, 2-fluorophenylacetyl, 3,4-dihydroxyphenylacetyl, 4-hydroxyphenylacetyl, 3-hydroxyphenylacetyl, 2,6-dimethoxyphenylacetyl, 3-carboxyphenylacetyl, 4-aminophenylacetyl, 3-ethoxyphenylacetyl, 4-methoxyphenylacetyl, 3,4-dimethoxyphenylacetyl, 4-t-butoxyphenylacetyl, 2-carboxyphenylacetyl, 3-chloro-4-methylphenylacetyl, 3- nitrophenylacetyl, and the like. When in the above formula m=1 and Z represents —O—, illustrative groups are the following. Phenoxyacetyl, 4-hydroxyphenoxyacetyl, 3-hydroxyphenoxyacetyl, 4-chlorophenoxyacetyl, 3-bromophenoxyacetyl, 3-ethylphenoxyacetyl, 4-methylphenoxyacetyl, 3-hydroxy-3-methylphenoxyacetyl, 4-aminophenoxyacetyl, 3-nitrophenoxyacetyl, 2-carboxyphenoxyacetyl, 2-chlorophenoxyacetyl, 4-t-butylphenoxyacetyl, 4-methoxyphenoxyacetyl, 3,4-dimethoxyphenoxyacetyl, 2-aminophenoxyacetyl, 4-isopropoxyphenoxyacetyl, 4-nitrophenoxyacetyl, and like acyl groups. When in the foregoing formula m=1 and Z represents —S—, illustrative groups are the following. Phenylmercaptoacetyl, 4-chlorophenylmercaptoacetyl, 3-hydroxyphenylmercaptoacetyl, 3,4-dimethylphenylmercaptoacetyl, 4-aminophenylmercaptoacetyl, 3,4-dichlorophenylmercaptoacetyl, 3-bromophenylmercaptoacetyl, 4-fluorophenylmercaptoacetyl, 2,6-difluorophenylmercaptoacetyl, 4-nitrophenylmercaptoacetyl, 3-fluorophenylmercaptoacetyl, and like groups.

When in formula I R' represents a group of the formula

illustrative acyl groups, R'—C=O, are the mandeloyl group of the formula

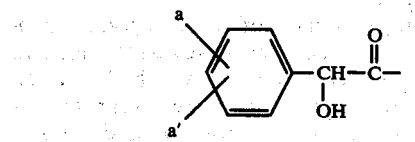

the α-carboxyphenylacetyl group represented by the following formula

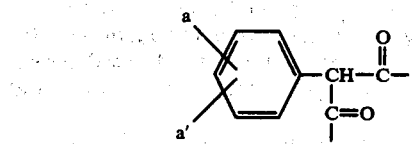

the α-sulfophenylacetyl group represented by the formula

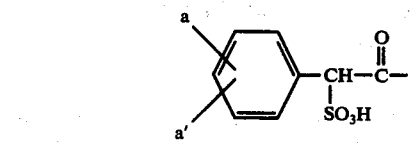

the phenylglycyl group represented by the formula

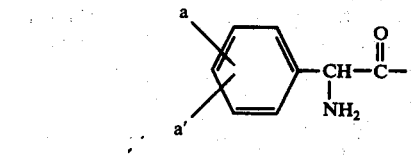

as well as those 2-thienyl and 3-thienyl acyl groups where in the above formula the phenyl group is replaced with a 2-thienyl or 3-thienyl ring.

Illustrative of the foregoing acyl groups are 4-methylmandeloyl, 4-hydroxymandeloyl, 3-hydroxymandeloyl, 4-aminomandeloyl, 3-bromomandeloyl, 4-chloromandeloyl, 3-methyl-4-fluoromandeloyl, 2-fluoromandeloyl, 4-fluoromandeloyl, 4-methoxymandeloyl, α-carboxy-4-methylphenylacetyl, α-carboxy-3,4-dichlorophenylacetyl, α-carboxy-4-hydroxyphenylacetyl, α-carboxy-3-hydroxyphenylacetyl, α-carboxy-4-aminophenylacetyl, α-sulfo-4-methylphenylacetyl, α-sulfo-3,4-dichlorophenylacetyl, α-formyloxy-2-thienylacetyl, α-sulfo-2-thienylacetyl, phenylglycyl, 4-hydroxyphenylglycyl, 3-chlorophenylglycyl, 3-hydroxyphenylglycyl, 4-methoxyphenylglycyl, α-amino-2-thienylacetyl, and α-amino-2-furylacetyl.

When in the foregoing formula R represents a group of the formula R''—CH$_2$—, illustrative acyl groups are the following: 2-thienylacetyl, 3-thienylacetyl, 2-furylacetyl, oxazalyl-2-acetyl, thiazolyl-2-acetyl, and tetrazalyl-1-acetyl.

The 3-(disubstituted-amino)cephalosporin esters of the above formula I are prepared by reacting a 7-amino- or 7-acylamino-3-cephem ester which is directly substituted in the 3-position by a halo or an alkyl or arylsulfonyloxy group with the cyclic or acyclic secondary amine HN(R$_2$)(R$_3$). The reaction is illustrated by the following reaction scheme.

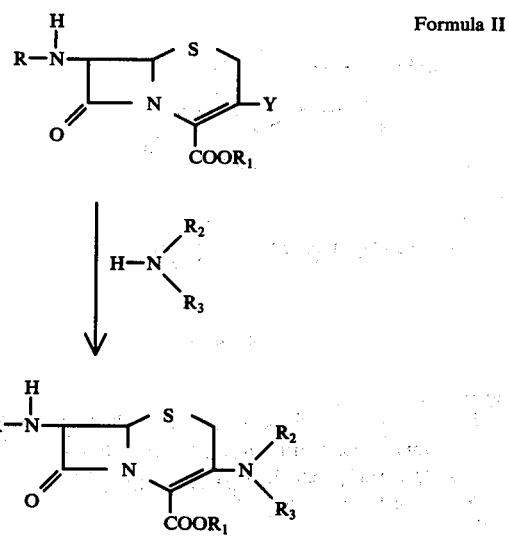

wherein R, R$_1$, R$_2$, and R$_3$ have the same meanings as defined in formula I and Y is halogen, preferably chloro or bromo, or an alkyl or arylsulfonyloxy group represented by the formula

—O—SO$_2$—R$_4$ wherein R$_4$ is C$_1$-C$_6$ alkyl, phenyl, halophenyl, or methylphenyl.

The reaction is carried out in a polar organic solvent at a temperature between about −5° and 35° C. and preferably at about 0° to 15° C. Two moles of the secondary amine per mole of 3-halo- or 3-sulfonyloxy-3-cephem ester are used and generally the amine is added somewhat in excess of two molar equivalents. Following the addition of the secondary amine the reaction mixture is stirred and is allowed to warm to room temperature. The reaction is generally completed over a period of between one to six hours.

Following the reaction, the product is extracted from the reaction mixture with an organic solvent such as ethyl acetate. For example, the reaction mixture is diluted with a mixture of brine and ethyl acetate with the product being extracted into the ethyl acetate. The extract is washed with brine and water and is dried and evaporated to yield the 3-(disubstituted-amino)-cephalosporin ester of the formula I.

Polar organic solvents which can be used in the reaction include for example, dimethylformamide (DMF), dimethylacetamide, pyrrolidone-2; the ether solvents of some polarity such as tetrahydrofuran, dioxane, and the diethers of glycols for example, the dimethylethers of ethylene glycol and propylene glycol and like solvents. Dimethylformamide is a preferred solvent.

The reaction is best carried out under anhydrous conditions; however, spurious amounts of water have no adverse effect. Accordingly, the solvent and secondary amine are preferably dried before use.

The secondary amines employed in the reaction are all known and are commercially available. Illustrative of the secondary amines represented by the formula $HN(R_2)(R_3)$ are the acyclic amines dimethylamine, diethylamine, di-n-proplylamine, di-n-butylamine, dibenzylamine, di-$\beta$-phenethylamine, N-methyl benzylamine, N-ethyl butylamine, N-methyl ethylamine, N-methyl iospropylamine, N-ethyl $\beta$-phenethylamine, N-n-propyl butylamine, and like acyclic secondary amines; the cyclic secondary amines pyrrolidine, piperidine, morpholine, thiomorpholine, 4-methylpiperazine, 4-ethylpiperazine, 4-n-butylpiperazine, and the like.

The 3-alkyl- or arylsulfonyloxy-3-cephem esters represented by the above formula II are prepared as described in my copending application Ser. No. 439,207, filed Feb. 6, 1974, now U.S. Pat. No. 3,985,737. As described therein a 7-acylamido-3-hydroxy-3-cephem-4-carboxylic acid ester is reacted with a $C_1$-$C_6$ alkylsulfonyl halide, a phenylsulfonyl halide, or a substituted phenylsulfonyl halide at a temperature between about $-5°$ and $35°$ C. in an aprotic solvent in the presence of a hydrogen halide acceptor. The 7-acylamido-3hydroxy3-cephem-4-carboxylic acid esters employed in the preparation of the 3-sulfonyloxy starting materials are prepared as described by R. R. Chauvette et. al., *J. Amer. Chem. Soc.*, 96, 4986 (1974). For example, a 3-hydroxy-3-cephem ester of the formula

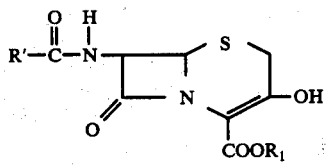

wherein R' and $R_1$ have the same meanings as defined for formula I, is reacted with an alkyl or arylsulfonyl halide in the presence of a tertiary amine or an alkylene oxide to provide the 3-sulfonyloxy ester of the above formula II wherein Y is the sulfonyloxy group —O—$SO_2$—$R_4$.

Representative of the alkyl and phenylsulfonyl halides which can be used are methanesulfonyl chloride, methanesulfonyl bromide, ethanesulfonyl chloride, n-butanesulfonyl chloride, n-hexanesulfonyl bromide, phenylsulfonyl chloride, p-chlorosulfonyl chloride, p-fluorosulfonyl chloride, p-toluenesulfonyl chloride, p-toluenesulfonyl bromide, 3- or 4-nitrobenzenesulfonyl chloride or bromide, 3-ethylbenzenesulfonyl chloride and 3-bromobenzenesulfonyl chloride or bromide.

Aprotic solvents which can be employed are the ether solvents such as tetrahydrofuran, dioxane and the dimethyl ether of ethylene glycol or like ether solvents. A preferred solvent which can be used is dimethylacetamide.

The reaction is carried out in the presence of a hydrogen halide acceptor such as an unreactive tertiary amine such as triethylamine or pyridine or an alkylene oxide, for example, propylene or butylene oxide. The preferred hydrogen halide acceptor is propylene oxide. The tertiary amine type acceptors tend to cause isomerization of the 3-cephem to a 2-cephem compound. With an alkylene oxide such isomerization is kept to a minimum with most sulfonyl halides.

The reaction is carried out by the addition of the stoichiometric amount of the sulfonyl halide, or a slight excess thereof, to a solution of the 3-hydroxy-3-cephem ester in the aprotic solvent containing at least a stoichiometric amount of the hydrogen halide acceptor. The reaction mixture is stirred and preferably between about $10°$ and $25°$ C. for between 3 and 12 hours. The sulfonate ester product is recovered from the reaction mixture by extraction with an organic solvent such as ethyl acetate or methylene chloride and is recovered from the extract. The 3-sulfonate esters can be purified by chromatography over silica gel.

When the starting material contains a functional group in the 7-acylamido side chain which is capable of reacting with the sulfonyl halide, the reactive group if protected with a suitable protecting group. For example, the $\alpha$-amino group of the phenylglycyl side chain can be protected during the sulfonyl ester formation with a variety of amino protecting groups. For example, the urethan protecting groups such as t-butyloxycarbonyl, 2,2,2-trichloroethoxycarbonyl, benzyloxycarbonyl, p-nitrobenzyloxycarbonyl, and the like: the enamine protecting groups formed with ethyl acetoacetate, acetyl acetone, and the like; the trityl group and other amino protecting groups. An amino substituent of a phenyl group in the 7-side chain can also be protected with the same groups. Likewise, an hydroxy group located in the 7-acylamido side chain, for example, in the mandeloyl side chain, is protected with a readily removable group such as, for example, the formyl group and the trichloroethoxycarbonyl group. Following the sulfonylation reaction such protecting groups are removed.

The foregoing description of the preparation of the sulfonate esters is illustrated in the following reaction scheme.

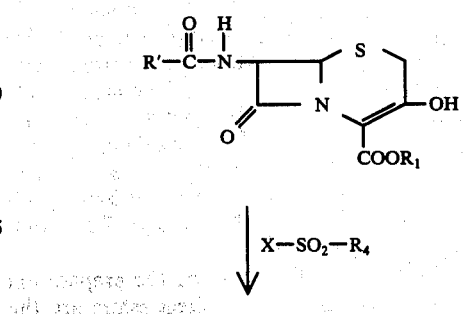

-continued

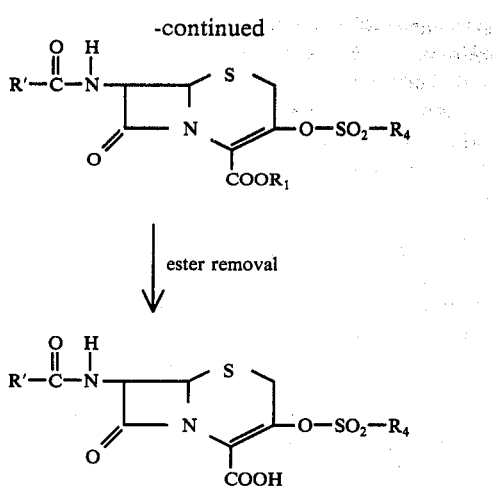

wherein R', R₁, and R₄ have the same meanings as previously defined.

The 3-hydroxy-3-cephem ester starting materials for the 3-sulfonyloxy-3-cephem esters are prepared by the ozonolysis of 3-exomethylenecepham esters which are described by R. R. Chauvette et al., in J. Amer. Chem. Soc., 38 2994 (1973).

The 3-halo-3-cephem esters represented by the above formula II when Y is chloro or bromo are also prepared with the 3-hydroxy-3-cephem esters as described by R. R. Chauvette et al., J. Amer. Chem. Soc., 96, 4986 (1974). For example, p-nitrobenzyl 7-[2-(2-thienyl)acetamido]-3-hydroxy-3-cephem-4-carboxylate is reacted with thionyl chloride in dry DMF to yield p-nitrobenzyl 7-[2-(2-thienyl)acetamido]-3-chloro-3-cephem-4-carboxylate.

Representative 3-alkyl and arylsulfonyloxy-3-cephem esters which can be used in the preparation of the 3-(disubstituted-amino)-3-cephem esters of this invention are p-nitrobenzyl 7-acetamido-3-methylsulfonyloxy-3-cephem-4-carboxylate, benzyl 7-phenoxyacetamido-3-methylsulfonyloxy-3-cephem-4-carboxylate, diphenylmethyl 7-phenylacetamido-3-ethylsulfonyloxy-3-cephem-4-carboxylate, diphenylmethyl 7-[2-(2-thienyl)acetamido]-3-(p-toluenesulfonyloxy)-3-cephem-4-carboxylate, p-methoxybenzyl 7-[2-(2-furyl)acetamido]-3-n-butylsulfonyloxy-3-cephem-4-carboxylate, diphenylmethyl 7-(D-mandelamido)-3-methanesulfonyloxy-3-cephem-4-carboxylate, p-nitrobenzyl 7-(D-phenylglycylamido)-3-methylsulfonyloxy-3-cephem-4-carboxylate, and phenacyl 7-benzamido-3-benzenesulfonyloxy-3-cephem-4-carboxylate.

Representative of the 3-halo-3-cephem ester starting materials are p-nitrobenzyl 7-[2-(2-thienyl)acetamido]-3-chloro-3-cephem-4-carboxylate, diphenylmethyl 7-phenylacetamido-3-bromo-3-cephem-4-carboxylate, p-nitrobenzyl 7-phenoxyacetamido-3-chloro-3-cephem-4-carboxylate, p-methoxbenzyl 7-(D-mandelamido)-3-chloro-3-cephem-4-carboxylate, p-nitrobenzyl 7-(D-phenylglycylamido)-3- chloro-3-cephem-4-carboxylate, diphenylmethyl 7-acetamido-3-chloro-3-cephem-4-carboxylate, t-butyl 7-[2-(phenyl)-2-(t-butyloxycarbonyl)acetamido]-3-chloro-3-cephem-4-carboxylate, phenacyl 7-benzamido-3-bromo-3-cephem-4-carboxylate, 2,2,2-trichloroethyl 7-phenoxyacetamido-3-chloro-3-cephem-4-carboxylate, and p-nitrobenzyl 7-amino-3-chloro-3-cephem-4-carboxylate.

The preferred starting materials for the preparation of the 3-(disubstituted-amino)-3-cephem esters are the 3-sulfonyloxy-3-cephem esters and in particular the methylsulfonyloxy-3-cephem esters.

To exemplify the preparation of a compound of this invention, diphenylmethyl 7-[2-(2-thienyl)acetamido]-3-methylsulfonyloxy-3-cephem-4-carboxylate is dissolved in dry DMF and the solution is cooled to about −5° c. Two molar C. of dry morpholine is added and the solution is then stirred at room temperature for about 4 hours. The product, diphenylmethyl 7-[2-(2-thienyl)acetamido]-3-morpholino-3-cephem-4-carboxylate is extracted from the reaction mixture and isolated from the extract.

In a further example, p-nitrobenzyl 7-phenoxyacetamido-3-methylsulfonyloxy-3-cephem-4-carboxylate is reacted in DMF at 0° C. with 2-molar equivalents of piperidine to provide after isolation, p-nitrobenzyl 7-phenoxyacetamido-3-piperidino-3-cephem-4-carboxylate.

When the 7-acyl group of the 3-halo or 3-sulfonyloxy-3-cephem ester contains an acidic function, e.g., in the formula I wherein Q is carboxy or a sulfo group, the acidic function is blocked by the formation of an ester derivative or is neutralized as the salt prior to reaction. Alternatively, an additional molar equivalent of the secondary amine reactant is employed in the reaction. Ester blocking groups which are suitable include those groups employed to block the C₄ carboxylic acid of the starting material as defined by R₁ in the formula I.

Representative 3-(disubstituted-amino)-3-cephem esters of the formula I are p-nitrobenzyl 7-phenoxyacetamido-3-dimethylamino-3-cephem-4-carboxylate, diphenylmethyl-7-[2-(2-thienyl)-acetamido]-3-pyrrolidino-3-cephem-4-carboxylate, p-methoxybenzyl 7-amino-3-piperidino-3-cephem-4-carboxylate, p-nitrobenzyl 7-amino-3-thiomorpholino-3-cephem-4-carboxylate, diphenylmethyl 7-[2-(2-furyl)acetamido]-3-diethylamino-3-cephem-4-carboxylate, phenacyl 7-acetamido-3-morpholino-3-cephem-4-carboxylate, p-nitrobenzyl 7-phenylacetamido-3-(4-methylpiperazino)-3-cephem-4-carboxylate, benzyl 7-(D-mandelamido-3-piperidino-3-cephem-4-carboxylate, diphenylmethyl 7-propionamido-3-diethylamino-3-cephem-4-carboxylate, p-nitrobenzyl 7-phenylacetamido-3-(N-methylbenzylamino)-3-cephem-4-carboxylate, p-methoxybenzyl 7-(4-chlorophenylacetamido)-3-(di-β-phenethylamino)-3-cephem-4-carboxylate, 2,2,2-trichloroethyl 7-phenoxyacetamido-3-morpholino-3-cephem-4-carboxylate, 2,2,2-trichloroethyl 7-(4-hydroxyphenylacetamido)-3-(N-methyl-n-butylamino)-3-cephem-4-carboxylate, p-nitrobenzyl 7-(D-phenylglycylamido)-3-morpholino-3-cephem-4-carboxylate, 2,2,2-trichloroethyl 7-(D-phenylglycylamido)-3-pyrrolidino-3-cephem-4-carboxylate, diphenylmethyl 7-[2-(1-tetrazolyl) acetamido]-3-piperidino-3-cephem-4-carboxylate, benzyl 7-[2-(2-thiazolyl)acetamido]-3-thiomorpholino-cephem-4-carboxylate, p-methoxybenzyl 7-[2-(2-oxazolyl)acetamido]-3-(4-ethylpiperazino)-3-cephem-4-carboxylate, and p-nitrobenzyl 7-amino-3-morpholino-3-cephem-4-carboxylate.

A preferred group of 3-(disubstituted-amino)-3-cephem esters of the formula I are the 3-cyclic secondary amino substituted esters wherein R₂ and R₃ are taken together to form pyrrolidino, piperidino, morpholino, and 4-methylpiperazino.

A further preferred group of compounds are represented by the formula I wherein

is phenoxyacetyl, phenylacetyl, 2-thienylacetyl, mandeloyl, phenylglycyl, or acetyl and —N($R_2$) ($R_3$) is pyrrolidino, piperidino or morpholino. Preferred ester groups of the term $R_1$ in formula I are diphenylmethyl, p-nitrobenzyl, and 2,2,2-trichloroethyl.

To illustrate the preparation of a preferred aminocephem ester, p-nitrobenzyl 7-phenoxyacetamido-3-exomethylenecepham-4-carboxylate is reacted in methanol with ozone at about −78° C. and the ozonide intermediate formed in situ is reduced with sodium bisulfite to afford p-nitrobenzyl 7-phenoxyacetamido-3-hydroxy-3-cephem-4-carboxylate. The 3-hydroxy ester is isolated from the reaction mixture and dissolved in DMF containing propylene oxide. A slight molar excess of methanesulfonylchloride is added with stirring to the solution to effect the sulfonylation of the 3-hydroxy group and provide p-nitrobenzyl 7-phenoxyacetamido-3-methylsulfonyloxy-3-cephem-4-carboxylate. The diester is dissolved in DMF, the solution cooled to −5° C. and two molar equivalents of morpholine are added with stirring. The reaction mixture is stirred at room temperature for 4 hours and the 3-amino ester product, p-nitrobenzyl 7-phenoxyacetamido-3-morpholino-3-cephem-4-carboxylate is recovered from the reaction mixture.

Representative of the preferred 3-amino esters of this invention are diphenylmethyl 7-[2-(2-(2-thienyl)acetamido]-3-pyrrolidino-3-cephem-4-carboxylate, p-nitrobenzyl 7-phenylacetamido-3-piperidino-3-cephem-4-carboxylate, p-nitrobenzyl 7-phenoxyacetamido-3-morpholino-3-cephem-4-carboxylate, diphenylmethyl 7-(D-mandelamido)-3-morpholino-3-cephem-4-carboxylate and p-nitrobenzyl 7-(D-phenylglycylamido)-3-morpholino-3-cephem-4-carboxylate.

The 3-(disubstituted-amino)-3-cephem esters can also be prepared with 3-acyloxy-3-cephem esters such as the 3-benzoyloxy or 3-acetoxy esters. Such acyl groups are eliminated with the secondary amines. The 3-acyloxy esters are prepared by acylating a 3-hydroxy ester.

The 3-(disubstituted-amino)-3-cephem esters of the formula I are useful intermediates for the preparation of 3-H-3-cephem antibiotic compounds represented by the formula

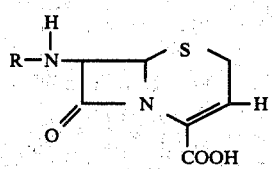

These 3-H-3-cephem antibiotics are described in W. German published application 2151567.

In one of its aspects this invention provides a process for converting the 3-(disubstituted-amino)-3-cephem esters of the formula I to the 3-H-cephem esters. According to the process a 7-amino- or 7-acylamido-3-(disubstituted-amino)-3-cephem ester of the formula I is reacted in an inert solvent with diborane to effect the reductive displacement of the 3-amino substituent and provide the 3-H-3-cephem ester. The reaction is carried out preferably at about room temperature although the reaction proceeds at a temperature between about 5° and 35° C. The reduction proceeds rapidly and is usually complete in about 1-2 hours.

The reduction is carried out under anhydrous conditions in inert solvents such as the ether solvents for example, tetrahydrofuran, dioxane, or the dimethylether of ethylene glycol. Tetrahydrofuran is a preferred solvent.

As in the preparation of the 3-amino esters of the formula I, an acidic function in the 7-position side chain (the 7-acylamido group) is blocked by forming an ester derivative thereof prior to reduction. For example, when the carboxylic acid function is present (formula I, Q = COOH), the carboxyl group is esterified.

The diphenylmethyl, p-nitrobenzyl or t-butyl ester derivatives serve as suitable blocking groups.

The diborane employed in the process is commercially available as a one molar solution in tetrahydrofuran. The required amount of diborane for use in the reduction is obtained by using the proper aliquot of the one molar tetrahydrofuran solution. An excess of diborane is used in the reaction.

Following the addition of the diborane, the reduction mixture is stirred for between 30 minutes and 2 hours and is then quenched by adding a suitable acid, for example, glacial acetic acid. The progress of the reduction can be followed chromatographically by withdrawing a small volume of the reaction mixture and after quenching, carrying out a thin layer chromatogram.

In an embodiment of the process, diphenylmethyl 7-phenoxyacetamido-3-morpholino-3-cephem-4-carboxylate is dissolved in dry tetrahydrofuran and a solution of diborane in THF containing in excess of one molar equivalent of diborane per mole of amino ester is added with stirring. After stirring for 1 hour, glacial acetic acid is added to the mixture. After the acidified reaction mixture is warmed for about 15 minutes on the steam bath, the reaction mixture is evaporated to remove THF and acetic acid. Alternatively, benzene can be added to the mixture and the acetic acid removed as the azeotrope with benzene. The residue is dissolved in a suitable organic solvent such as ethyl acetate and the solution is washed with brine and dried. The dried solution is evaporated to yield the reaction product, diphenylmethyl 7-phenoxyacetamido-3H-3-cephem-4-carboxylate.

The following reaction scheme illustrates the foregoing reduction process.

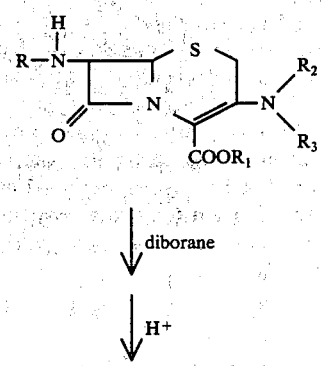

Formula III

-continued

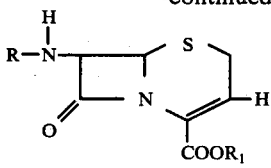

wherein R is an acyl group

and R', $R_1$, $R_2$, and $R_3$ have the same meanings as defined for the formula I.

Following the reduction of the 3-(disubstituted-amino)-cephem ester the $C_4$ ester group of the 3H-3-cephem ester (III) is removed by known methods to obtain the free carboxylic acid antibiotic compound. For example, the p-nitrobenzyl ester group is removed via catalytic hydrogenolysis over palladium on carbon (U.S. Pat. No. 3,632,850); the diphenylmethyl group (benzhydryl) is removed with trifluoroacetic acid in anisole at about 10° C.; the p-methoxybenzyl group is removed with trifluoroacetic acid at about 10° C. [*J. Org. Chem.*, 36, 1259 (1971)]; the 2,2,2-trichloroethyl group is removed with zinc and acid [*J. Am. Chem. Soc.*, 88, 852 (1966)]; the benzyl ester group is removed via catalytic hydrogenolysis over palladium catalyst [U.S. Pat. No. 3,197,466, *J. Org. Chem.*, 27, 1381 (1962)]; and the tert-butyl group is removed as described in *J. Org. Chem.*, 31, 444 (1966).

Representative 3H-3-cephem antibiotics prepared by the process are 7-acetamido-3H-3-cephem-4-carboxylic acid, 7-[2-(2-thienyl)acetamido]-3H-3-cephem-4-carboxylic acid, 7-phenylacetamido-3H-3-cephem-4-carboxylic acid, 7-(D-mandelamido)-3H-3-cephem-4-carboxylic acid, 7-phenylmercaptoacetamido-3H-3-cephem-4-carboxylic acid, 7-propionamido-3H-3-cephem-4-carboxylic acid and 7-[2-(phenyl)-2-(carboxy)acetamido]-3H-3-cephem-4-carboxylic acid.

The 3-(disubstituted-amino)-3-cephem esters of the formula I are also useful in the preparation of 3-aryl- and 3-alkyl-3-cephem antibiotic compounds. According to a further aspect of this invention, there is provided a process for preparing 3-aryl-, e.g., 3-phenyl; and 3-alkyl-, e.g., 3-methyl, 3-cephem-4-carboxylic acids, which comprises reacting an amino ester of the formula I with an aryl or alkyl Grignard reagent in an inert solvent at a temperature between about −80° and 5° C. The reaction proceeds via addition of the Grignard reagent across the $\Delta^3$ double bond to form a 3-aryl- or 3-alkyl-3-(di-substituted-amino)cephem-4-carboxylic acid ester. The 3,3-disubstituted cephem ester can be isolated or alternatively it is treated with acid such as formic acid, acetic acid, or trifluoroacetic acid to yield after isolation the 3-alkyl- or 3-aryl-3-cephem ester.

Most Grignard reagents will react with compounds of the Formula I to provide the corresponding 3-aryl or 3-alkyl-3-cephem ester. Certain Grignard reagents are preferred, however. These reagents are represented by the following formula BrMgR$_5$ wherein $R_5$ is $C_1$-$C_4$ lower alkyl or phenyl.

The process is illustrated by the following reaction scheme wherein $R_5$ is ethyl and R', $R_1$, $R_2$, and $R_3$ are as defined for the formula I.

Formula IV

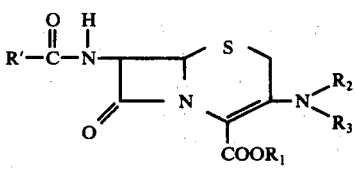

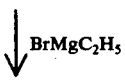

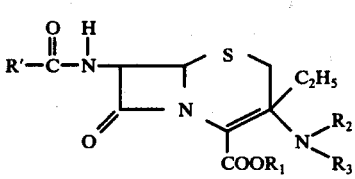

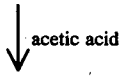

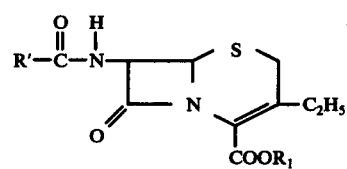

Solvents which can be used in the process are the ether-type solvents such as tetrahydrofuran, dioxane, diglyme, and the like. THF is a preferred solvent.

The Grignard reagents BrMgR$_5$ are all known compounds readily prepared by conventional methods. Representative reagents include methylmagnesium bromide, ethylmagnesium bromide, n-propylmagnesium bromide, iso-propylmagnesium bromide, n-butylmagnesium bromide, and phenylmagnesium bromide.

In one embodiment of the process, p-nitrobenzyl 7-phenylacetamido-3-morpholino-3-cephem-4-carboxylate is dissolved in THF and the solution cooled to about −78° C. A diethyl ether solution of phenylmagnesium bromide is added to the cold solution with stirring. After about 1 hour the reaction mixture is acidified with glacial acetic acid and is allowed to warm to room temperature. The mixture is then heated on the steam bath for about 10 minutes and is then evaporated to dryness. The product, p-nitrobenzyl 7-phenylacetamido-3-phenyl-3-cephem-4-carboxylate, is extracted from the residue with ethyl acetate.

Representative 3-alkyl- and 3-phenyl-3-cephem esters and acids prepared in the process of this invention are p-nitrobenzyl 7-acetamido-3-methyl-3-cephem-4-carboxylate, 7-benzamido-3-ethyl-3-cephem-4-carboxylic acid, 7-[2-(2-furyl)acetamido]-3-phenyl-3-cephem-4-carboxylic acid, 7-(D-mandelamido)-3-phenyl-3-cephem-4-carboxylic acid, diphenylmethyl 7-phenylmercaptoacetamido-3-ethyl-3-cephem-4-carboxylate, 7-[2-(phenyl)-2-(carboxy)acetamido]-3-phenyl-3-cephem-4-carboxylic acid, and like 3-alkyl and 3-phenyl esters and carboxylic acids.

The following examples further illustrate the compounds of the invention and their methods of preparation and usefulness as intermediates in the processes to antibiotic compounds.

EXAMPLE 1 p-Nitrobenzyl
7-[2-(2-thienyl)acetamido]-3-methylsulfonyloxy-3-cephem-4-carboxylate To a solution of 4.75 g. (10 mmole) of p-nitrobenzyl 7-[2-(2-thienyl)acetamido]-3-hydroxy-3-cephem-4-carboxylate in 50 ml. of dry dimethylacetamide were added 2 ml. of propylene oxide. To the solution was added with stirring one equivalent of methanesulfonyl chloride and stirring was continued for 3 hours. The reaction mixture was then taken up in ethyl acetate and the solution was washed with a saturated solution of sodium chloride. The washed organic phase was evaporated in vacuo to dryness to obtain the reaction product mixture as a residue. The reaction product was purified by preparative thin layer chromatography on silica gel using for elution 65 percent ethyl acetate/hexane.

The purified product gave the following percent elemental composition on microanalysis.

Calculated for $C_{21}H_{19}N_3O_9S_3$: Theory: C, 45.56; H, 3.46; N, 7.59; S, 17.38. Found: C, 45.74; H, 3.56; N, 7.30; S, 17.06.

The nuclear magnetic resonance spectrum and the infrared absorption spectrum were in agreement with the structure of the product formed.

N.M.R. (DMSO $d_6$) delta values: 3.47 (s, 3H, methyl); 3.80 (broad s, 2H, side chain $CH_2$); 3.91 (q, 2H, $C_2H_2$); 5.29 (d, 1H, $C_6H$); 5.46 (broad s, 2H, ester $CH_2$); 5.84 (q, 1H, $C_7H$); 6.86–7.44 (m, 3H, thiophene); and 7.98 (q, 4H, phenyl).

I.R. (mull) 1785, 1350, and 1158 $cm^{-1}$

U.V. (ethanol) λ max 264 mμ.

The above product (2 g.) was dissolved in a solvent mixture of 15 ml. of methanol and 20 ml. of tetrahydrofuran and 3 g. of prereduced 5 percent palladium on carbon catalyst were added. (The catalyst had been prereduced in 15 ml. of methanol for 1 hour prior to use.) The mixture was hydrogenated for 1.5 hours during which time the theoretical hydrogen uptake had occurred.

The catalyst was filtered and the filtrate was evaporated to dryness on a rotary evaporator in vacuo. The residue was dissolved in 20 ml. of ethyl acetate and 20 ml. of cold water were added. The pH of the solution was adjusted to pH 7 with a solution of sodium bicarbonate and the organic layer was separated. Ethyl acetate was layered over the aqueous phase and the pH adjusted to 2.0 with 1N hydrochloric acid. The organic layer was separated and combined with an ethyl acetate extract of the acidified aqueous layer. The combined extract and organic layer were dried over magnesium sulfate and evaporated to dryness to yield the de-esterified product, 7-[2-(2-thienyl)acetamido]-3-methylsulfonyloxy-3-cephem-4-carboxylic acid.

N.M.R. (acetone $d_6$) delta values: 3.33 (s, 3H, methyl; 3.50–4.00 (m, 4H, two $CH_2$); 5.10 (d, 1H, $C_6H$); 5.88 (d, 1H, $C_7H$); 6.80–7.40 (m, 3H, thiophene).

I.R. (KBr) 1795, 1175 $cm^{-1}$

U.V. (ethanol) λ max 265 mμ. (shoulder)

Electrometric titration (80 percent aqueous methyl cellosolve) $pK_a$ 3.9.

EXAMPLE 2

Preparation of diphenylmethyl
7-[2-(2-thienyl)acetamido]-3-morpholino-3-cephem-4-carboxylate To a solution of 1.170 g. (2 mmole) of diphenylmethyl 7-[2-(2-thienyl)acetamido]-3-methylsulfonyloxy-3-cephem-4-carboxylate in 10 ml. of dry DMF cooled to about −5° C. in an ethanol-ice bath were added with stirring 4 mmoles (0.348 ml.) of dry morpholine. The reaction mixture was allowed to warm slowly to room temperature and after 4 hours the product was extracted from the reaction mixture with a mixture of ethyl acetate and brine. The ethyl acetate layer was separated, dried, and evaporated to yield 1.277 g. of crude product. The product was recrystallized from ethyl acetate to yield 0.825 g.

Elemental analysis for $C_{30}H_{29}N_3O_5S_2$: Theory: C, 62.59; H, 5.08; N, 7.30. Found: C, 62.77; H, 5.17; N, 7.18.

N.M.R. ($CDCl_3$): 2.5–3.7 (10H, m; morpholino and 2-position $CH_2$), 3.95 (2H, s; amide $CH_2$), 5.05 (1H, d, J = 4.5 Hz; 6-position H), 5.48 (1H, d/d J = 4.5, 9.0 Hz; H at 7-position), 6.60 (1H, s; ester methine), 6.85–7.60 (13H, m; ester aromatic and thiophene) and 8.05 (1H, d, J = 9.0; amide NH) delta.

U.V. (ethanol) λ max 338 nm, ε = 11,380.

The infrared absorption spectrum of the product showed two prominent bands at 1750 and 1670 $cm^{-1}$.

EXAMPLE 3

Diphenylmethyl
7-[2-(2-thienyl)acetamido]-3-piperidino-3-cephem-4-carboxylate.

By employing the procedures and starting material of Example 2 and substituting piperidine for morpholine the title compound was prepared.

Elemental analysis for $C_{32}H_{33}N_3O_4S_2$: Theory: C, 65.39; H, 5.66; N, 7.15. Found: C, 64.49; H, 5.71; N, 6.73.

U.V. absorption (ethanol): λ max = 308 nm; ε = 16,330

EXAMPLE 4 p-Nitrobenzyl
7-[2-(2-thienyl)acetamido]-3-pyrrolidino-3-cephem-4-carboxylate

To a solution of 0.988 g. (2 mmole) of p-nitrobenzyl 7-[2-(2-thienyl)acetamido]-3-chloro-3-cephen-4-carboxylate in 10 ml. of dry DMF maintained at ice-bath temperature were added 0.375 ml. (4.4 mmole) of pyrrolidine. The reaction mixture was allowed to stir for about 1 hour and the mixture was then diluted with brine and ethyl acetate. The ethyl acetate was washed with brine several times and dried over magnesium sulfate. Evaporation of the dried extract gave 845 mg. of product.

N.M.R. ($CDCl_3$): 1.4–2.4 (4H, m; pyrrolidino), 2.6–4.1 (8H, m; amide $CH_2$, 2-position $CH_2$ and pyrrolidino), 4.9–5.7 (4H, m; β-lactam 6- and 7-H, and ester $CH_2$), 6.9–7.1 (2H, m; thiophene), 7.1–7.3 (1H, m; thiophene), 7.60 (2H, d, J = 9.0; ester aromatic) and 8.2 (2H, d, J = 9.0; ester aromatic), and amide NH occurs under the doublet (d) at 8.2 delta.

EXAMPLE 5 p-Nitrobenzyl 7-phenylacetamido-3-bromo-3-cephem-4-carboxylate is reacted with dimethylamine by following the reaction conditions of Example 4 to provide p-nitrobenzyl 7-phenylacetamido-3-dimethylamino-3-cephem-4-carboxylate.

EXAMPLE 6 p-Methoxybenzyl 7-phenoxyacetamido-3-diethylamino-3-cephem-4-carboxylate is prepared with p-methoxybenzyl 7-phenoxyacetamido-3-ethylsulfonyloxy-3-cephem-4-carboxylate and diethylamine in THF.

EXAMPLE 7

Diphenylmethyl 7-[2-(2-thienyl)acetamido]-3H-3-cephem-4-carboxylate

To a solution of 0.576 g. (1 mmole) of diphenylmethyl 7-[2-(2-thienyl)acetamido]-3-morpholino-3-cephem-4-carboxylate in 20 ml. of THF were added by syringe 2 ml. of a one molar solution of diborane in THF. The reaction mixture was stirred for 1 hour at room temperature and 15 ml. of glacial acetic acid were added. The mixture was then heated on the steam bath for about 15 minutes and was evaporated in vacuo with a little added benzene. The residue was dissolved in 150 ml. of ethyl acetate with a small volume of a saturated solution of sodium bicarbonate. The solution was washed 4 times with brine and was dried. The dry solution was evaporated in vacuo to yield 0.406 g. of the crude product.

The product was purified via preparative thin layer chromatography using 40 percent acetone in ethyl acetate for elution to obtain 0.067 g. of the product.

N.M.R. (CDCl$_3$): 3.0–3.3 (2H, m; 2H at 2-position), 3.6 (2H, s; CH$_2$ of amide), 4.6 (1H, d, J = 5 Hz; H at 6-position), 5.7 (1H, d/d, J = 5.0, 9.0; H at 7-position), 6.3–6.7 (1H, m; vinyl H) and 6.7–7.5 (15H, m; ester methine, ester aromatic, thiophene and amide NH) delta.

The product was treated with 0.2 ml. of anisole and 0.4 ml. of trifluoroacetic acid for 6 minutes to remove the diphenylmethyl group. The mixture was diluted with 50 ml. of acetone and the solution evaporated in vacuo. The residue was dissolved in ethyl acetate and the solution was given an acid-base wash and then dried over magnesium sulfate. The dried solution was evaporated to yield 24 mg. of 7-[2-(2-thienyl)-acetamido]-3H-3-cephem-4-carboxylic acid.

EXAMPLE 8

A solution of 306 mg. (0.53 mmole) of diphenylmethyl 7-[2-(2-thienyl)acetamido]-3-morpholino-3-cephem-4-carboxylate in 230 ml. of the THF was cooled to about 0°–5° C. and 0.368 ml. of a 2.88 molar solution of ethylmagnesium bromide in diethyl ether were added. The reaction was stirred in the cold for 45 minutes and then about 15 ml. of glacial acetic acid were added to the mixture. The acidified mixture was heated on the steam bath for 10 minutes, was cooled and benzene was added. The mixture was evaporated to dryness and the residue was dissolved in ethyl acetate. The ethyl acetate solution was washed with brine, dried and evaporated to dryness. The product, diphenylmethyl 7-[2-(2-thienyl)acetamido]-3-ethyl-3-cephem-4-carboxylate, is purified by chromatography over silica gel using ethyl acetate:acetone, 1:1, v:v for elution.

The nuclear magnetic resonance spectrum of the 3-ethyl ester showed the following signals:

N.M.R. (CDCl$_3$): 1.0 (3H, t, J = 8.0; methyl), 2.1 (2H, q, J = 8.0; allylic CH$_2$), 3.5–4.0 (4H, m; 2H at 2-position and amide CH$_2$), 5.1 (1H, d, J = 5.0 Hz; H at 6-position), 5.5 (1H, d/d, J = 5.0, 9.0 Hz; H at 7-position), 6.7 (1H, d, J = 9.0 Hz; amide NH) and 6.9–7.5 (14H, m, aromatic H and ester CH group) delta.

The ethyl diphenylmethyl ester product was treated with a mixture of 0.2 ml. of anisole and 0.4 ml. of 90 percent formic acid for 6 minutes at room temperature to effect the removal of the diphenylmethyl ester group to yield 9 mg. of 7-[2-(2-thienyl)acetamido]-3-ethyl-3-cephem-4-carboxylic acid.

N.M.R. (CDCl$_3$) 1.0 (3H, t, J = 8.0; methyl), 2.1–2.6 (2H, m; allylic CH$_2$), 3.4–4.0 (4H, m; 2H at (2-position, amide CH$_2$), 5.1 (1H, d, J = 5.0 Hz; H at 6-position), 5.5 (1H, d/d, J = 5.0, 9.0 Hz; H at 7-position) and 6.4–7.6 (5H, m; thiophene, amide NH, carboxyl H) delta.

EXAMPLE 9

7-[2-(2-Thienyl)acetamido]-3-phenyl-3-cephem-4-carboxylic acid

By following the procedures described by Example 8 and substituting phenylmagnesium bromide for ethylmagnesium bromide, diphenylmethyl 7-[2-(2-thienyl)acetamido]-3-phenyl-3-cephem-4-carboxylate was prepared.

N.M.R. (CDCl$_3$): 3.6–4.0 (4H, m; 2H at 2-position, amide CH$_2$), 5.3–5.7 (2H, m; β-lactam 6-and 7-position H), 6.7 (1H, d, J = 9.0 Hz; amide NH) and 6.8–7.6 (19H, m; aromatic H and ester methine) delta.

The diphenylmethyl ester group was removed with a mixture of anisole and trifluoroacetic acid to yield 3-phenyl-3-cephem acid compound.

N.M.R. (CDCl$_3$): 3.6–4.1 (4H, m; amide CH$_2$, and 2-position CH$_2$), 5.3–5.7 (2H, m; β-lactam 6- and 7-position H), 6.7–7.4 (8H, m, aromatic H and amide NH) and 7.7 (1H, broad s; carboxyl H) delta.

I claim:

1. The process for preparing a 3-alkyl or 3-phenyl-3-cephem ester of the formula

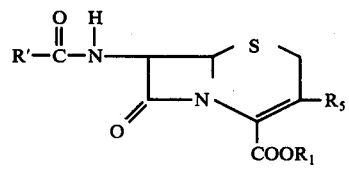

which comprises (1) reacting a compound of the formula

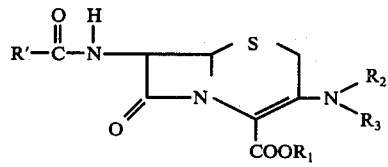

in an inert ether solvent at a temperature between about −80° and 5° C. with the Grignard reagent BrMgR$_5$ wherein R$_5$ is C$_1$–C$_4$ alkyl, or phenyl, (2) acidifying the reaction mixture and (3) separating the 3-alkyl- or 3-phenyl-3-cephem ester from the reaction mixture; where in the above formulas R' is C$_1$–C$_6$ alkyl, C$_1$–C$_3$ cyanoalkyl, phenyl, halophenyl, methylphenyl, hydroxyphenyl, nitrophenyl, aminophenyl, or methoxyphenyl; or R' is a group of the formula

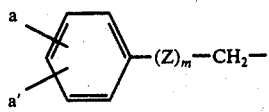

wherein $a$ and $a'$ are independently hydrogen, $C_1$-$C_4$ alkyl, $C_1$-$C_4$ alkoxy, halogen, nitro, amino, or carboxy, Z is O or S, and $m$ is 0 or 1; or R' is a group of the formula

wherein P is thienyl, phenyl or

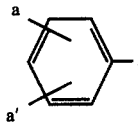

wherein $a$ and $a'$ are as defined above; Q is hydroxy, amino, carboxy or —$SO_3H$; or R' is a group of the formula

R''—$CH_2$— wherein R'' is thienyl, furyl, 2-oxazolyl, 2-thiazdyl, or 1-tetrazdyl; $R_1$ is benzyl, 4-nitrobenzyl, 4-methoxybenzyl, diphenylmethyl, t-butyl or 2,2,2-trichloroethyl; and $R_2$ and $R_3$ when taken separately are independently $C_1$-$C_4$ alkyl, benzyl or phenethyl, and when taken together with the attached nitrogen are pyrrolidino, piperidino, morpholino, thiomorpholino or a 4-substituted piperazino group of the formula

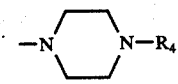

wherein $R_4$ is $C_1C_4$ lower alkyl.

2. The process of claim 1 wherein the solvent is tetrahydrofuran.

3. The process of claim 2 wherein R'(CO)— is thienylacetyl, phenylacetyl, or phenoxyacetyl.

4. The process of claim 3 wherein $R_1$ is diphenylmethyl or p-nitrobenzyl.

5. The process of claim 3 wherein $R_2$ and $R_3$ are pyrrolidino, piperidino, morpholino or a 4-substituted piperazino group.

* * * * *